(12) United States Patent
Lee et al.

(10) Patent No.: US 6,235,920 B1
(45) Date of Patent: May 22, 2001

(54) METHOD FOR PREPARING FUNCTIONAL HALOSILANES

(75) Inventors: Michael Kang-Jen Lee; Aroop Kumar Roy, both of Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/356,018

(22) Filed: Jul. 19, 1999

(51) Int. Cl.$^7$ ............................................ C07F 7/08
(52) U.S. Cl. .................. 556/404; 556/405; 556/427; 556/428; 556/436; 556/440; 549/4; 549/6; 549/214; 546/14
(58) Field of Search ............................. 556/409, 405, 556/436, 440, 427, 428; 549/214, 4, 6; 546/14

(56) References Cited

U.S. PATENT DOCUMENTS

| | | | |
|---|---|---|---|
| 5,082,958 | 1/1992 | Wright | 556/413 |
| 5,290,901 | 3/1994 | Burns | 528/34 |
| 5,693,826 | * 12/1997 | Tanaka et al. | 556/404 X |
| 5,705,665 | * 1/1998 | Ichinohe et al. | 556/428 |

OTHER PUBLICATIONS

Journal of Organometallic Chemistry, 80 (Aug. 1974) 47–69.
Journal of Organomettalic Chemistry, 114 (Jun. 1976) 21–33.
Chemical Abstracts, vol. 118, no. 23, 7 Jun. 1993. Abstract no. 234123, Volkova, L.M., et. al. "Synthesis of (acyloxy)butychlorodimethylsilanes, bis(acyloxy)butyl tetramethyldisiloxanes, and some of their derivatives".
Chemical Abstracts, vol. 91, no. 7, 13 Aug. 1979. Abstract no. 57101, Andrianov, K. A., et. al. "synthesis of diorganosilaoxacyclohexanes and acyloxybutyldiorganochlorosilanes from them."
Chemical Abstracts, vol. 79, no. 21, 26 Nov. 1973. Abstraction no. 126605, Andrianov, K.A., et. al. "Dimethl (acyloxybutyl)chlorosilanes."
Chemical Abstracts, vol. 92, no. 13, 31 Mar. 1980. Abstract no. 110172, Andrianov, K.A. et. al., "Reaction of 1,1–dimethyl–1sila–2–oxacyclohexane with organic acids."
J. Organomet. Chem., vol. 114, no. 1, 1976 "Oxasilacycloalkanes: synthesis and reactivity with respect to nucleophilic reagents and carbonyl derivatives."

* cited by examiner

Primary Examiner—Paul F. Shaver
(74) Attorney, Agent, or Firm—Alex Weitz

(57) ABSTRACT

The present invention relates to a method for preparing a functional halosilanes by reacting
A) a cyclic silyl ether having the formula

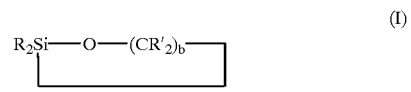

(I)

wherein each R is independently selected from a hydrocarbyl group or a halogen-substituted hydrocarbyl group having 1 to 20 carbon atoms, each R' is independently selected from a group consisting of hydrogen and R and b is 3, 4 or 5; and
(B) a halogen-functional compound having a formula selected from

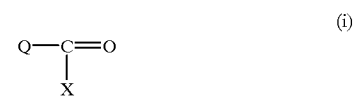

(i)

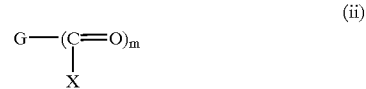

(ii)

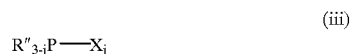

(iii)

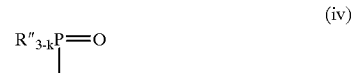

(iv)

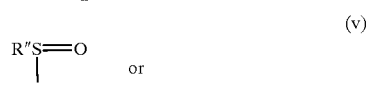

(v)

or

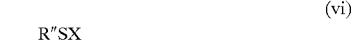

(vi)

wherein Q is a monovalent group having 2 to 20 carbon atoms selected from alkenyl groups, aralkenyl groups or a heterocyclic hydrocarbyl group having oxygen, nitrogen or sulfur hetero atoms in its ring, G is an m-valent organic group, m is at least 2, X is halogen, R" is independently selected from hydrocarbyl groups or halogen-substituted hydrocarbyl groups having 1 to 20 carbon atoms, j is an integer having a value of 1 to 3 and k is an integer having a value of 1 to 3.

10 Claims, No Drawings

METHOD FOR PREPARING FUNCTIONAL HALOSILANES

FIELD OF THE INVENTION

The present invention relates to a method for preparing functional halosilanes. More particularly, the invention relates to a method for reacting a cyclic silyl ether with certain halogen-functional compounds.

BACKGROUND OF THE INVENTION

Organofunctional silanes, such as aminoalkyl-, mercaptoalkyl-, phosphinoalkyl-, and the like, represent an important class of silicon compounds. These silanes find extensive application in commercial products such as coupling agents, adhesion promoters and crosslinkers, inter alia. These compounds can also be used to functionalize siloxane polymers, thereby enhancing their advantageous properties in various silicone applications.

A number of existing methods for preparing organofunctional silanes depend on multi-step synthetic routes that suffer from poor yield and waste problems in one or more of the steps. For example, preparation of acid chloride functional silanes requires a two-step process wherein a carboxy acid-functional silane is first synthesized and this, in turn, is reacted with thionyl chloride. The latter compounds find utility in the preparation of silicone-organic copolymers and organofunctional silanes that can be derived from their well-known reactivity. There is, therefore, a need for improved methods which can provide various functional silanes in an efficient and economical manner.

A simple method for preparing carbinol-functional siloxanes has been disclosed by Burns et al. in U.S. Pat. No. 5,290,901. In this procedure, a cyclic silyl ether is reacted with an organosiloxane or organosiloxane resin. The reactivity of such a cyclic silyl ether was studied by R. J. P. Corriu et al. (*Journal of Organometallic Chemistry*, 114, 21–33 (1976)) and these authors disclose the reaction of an oxasilacyloalkane with acetyl chloride to form an acetate-functional chlorosilane.

However, there is no expectation that the outcome of the reaction of a cyclic silyl ether with any given halogen-functional component, other than the simple acyl halide illustrated by Corriu et al., could be predicted without experimentation. Thus, neither the publication by Corriu et al. nor any other prior art know to applicants teaches the reaction of such cyclic silyl ethers with the particular halogen-functional compounds of the present invention to prepare functional halosilanes.

SUMMARY OF THE INVENTION

It has now been discovered that several classes of organofunctional silanes can be prepared in high yields by reacting a cyclic silyl ether and certain activated halogen compounds. Surprisingly, even closely related structures to the select halogen-functional compounds of the invention did not react with the cyclic silyl ether. The products of reaction find utility as intermediates for the preparation of silicone polymers and silicone-organic copolymers, formation of supported catalysts and for use in surface modification.

The present invention, therefore, relates to a method for preparing a functional halosilanes by reacting (A) a cyclic silyl ether having the formula

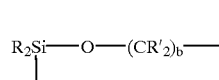

(I)

wherein each R is independently selected from a hydrocarbyl group or a halogen-substituted hydrocarbyl group having 1 to 20 carbon atoms, each R' is independently selected from a group consisting of hydrogen and R and b is 3, 4 or 5; and
(B) a halogen-functional compound having a formula selected from

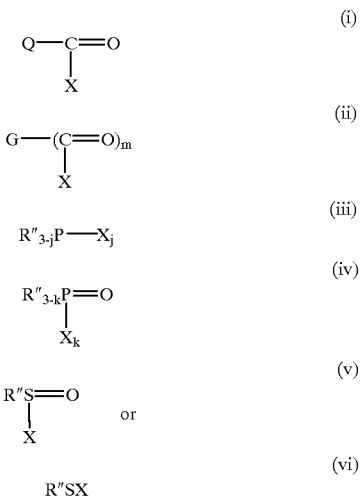

wherein Q is a monovalent group having 2 to 20 carbon atoms selected from alkenyl groups, aralkenyl groups or a heterocyclic hydrocarbyl group having oxygen, nitrogen or sulfur hetero atoms in its ring, G is an m-valent organic group, m is at least 2, X is halogen, R" is independently selected from hydrocarbyl groups or halogen-substituted hydrocarbyl groups having 1 to 20 carbon atom, j is an integer having a value of 1 to 3 and k is an integer having a value of 1 to 3.

The invention also relates to the products formed by the above described reactions.

DETAILED DESCRIPTION OF THE INVENTION

In the method of the present invention, a cyclic silyl ether represented by formula (I) is reacted with one of the halogen-functional compounds represented by formulas (i) through (vi).

Cyclic silyl ether (A) has the formula (I)

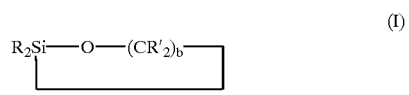

(I)

wherein each R is independently selected from monovalent hydrocarbyl groups or halogen-substituted hydrocarbyl groups having 1 to 20 carbon atoms, with the proviso that R can not have terminal (i.e., vinylic) unsaturation. Each unsubstituted R group can be an alkyl group having 1 to 20 carbon atoms, a cycloalkyl group having 3 to 10 carbon atoms, an alkenyl group having 3 to 20 carbon atoms or an aryl group having 6 to 20 carbon atoms. Specific non-limiting examples of R groups include methyl, ethyl, propyl, isopropyl, butyl, tert-butyl, pentyl, cyclopropyl, cyclopentyl, benzyl, beta-phenylethyl, gamma-tolylpropyl, phenyl, tolyl, xylyl, and naphthyl. For the purposes of the present invention, the groups R and R' must be inert with respect to the reaction between components (A) and (B), further described infra. Non-limiting examples of substituted groups may be illustrated by chloropropyl, 3,3,3-trifluoropropyl, perfluoropropyl, chlorophenyl, pentafluorophenyl and nonafluorobutyl. In formula (I), each R' is independently selected from hydrogen or the above described R group and b is 3, 4 or 5.

Preferably, component (A) has one of the following structures

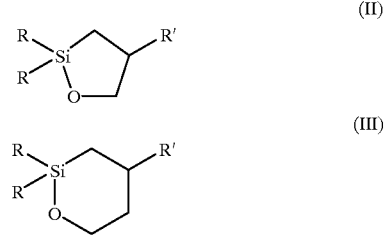

wherein R and R' have their previously defined meanings. In formulas (II) and (III) each R is preferably independently selected from methyl, phenyl or trifluoropropyl (i.e., $CF_3CH_2CH_2-$) and R' is either hydrogen or methyl. Most preferably, R and R' is each methyl. A particularly preferred component (A) is 2,2,4-trimethyl-1-oxa-2-silacyclopentane having the structure

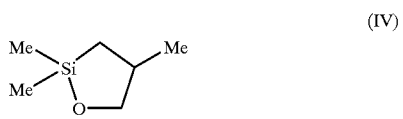

wherein Me hereinafter denotes a methyl group.

The above described cyclic silyl ethers are known in the art and may be prepared by methods reviewed in, e.g., U.S. Pat. No. 5,290,901.

In a first embodiment of the present invention, the above described cyclic silyl ether (A) is reacted with an acyl halide of the formula

wherein Q is a monovalent group having 2 to 20 carbons selected from alkenyl groups, aralkenyl groups or a heterocyclic hydrocarbyl group which contains at least one oxygen, nitrogen or sulfur hetero atom in its ring with the proviso that these heterocyclic groups do not react with component (A). In formula (i), X is a halogen group selected from fluorine, chlorine, bromine or iodine, preferably chlorine. For the purposes of this first embodiment, the carbon-carbon double bond (i.e., —C═C—) of Q is preferably conjugated with the —C═O group of component (i). The Q group may be illustrated by vinyl, isopropenyl, allyl, hexenyl, 2-furonyl, acryl, methacryl, 2-phenylethyl, 2-thiophene and 2-quinoxalinyl, inter alia. Particularly preferred Q groups are vinyl and isopropenyl. Specific examples of component (i) include acryloyl chloride, methacryloyl chloride, cinnamoyl chloride, 2-furoyl chloride, 2-thiophene carbonyl chloride, 2-thiopheneacetyl chloride, 2-quinoxaloyl chloride and nicotinoyl chloride.

Compounds represented by formula (i) are known in the art and specific preferred compounds according to the first embodiment include acryloyl chloride, methacryloyl chloride and cinnamoyl chloride.

The reaction between components (A) and (i) can be carried out either neat or in a non-reactive organic solvent such as toluene, hexane, dibutyl ether or cyclohexane, typically at a temperature of about 0 to 150° C. These components are generally combined so as to provide about one equivalent of acid halide group for each equivalent of the cyclic silyl ether. Preferably, the reaction is conducted without solvent at a temperature of 20 to 100° C. Although stoichiometric quantities of (A) and (i) can be used (i.e., one equivalent of component (A) to one equivalent of component (i)), it is preferred to use an excess of up to about 25% of component (i). As mentioned above, it was surprisingly observed that closely related acyl halide compounds, such as allyl chloroformate, and halide-functional hydrocarbons, such as allyl chloride, did not react with the cyclic silyl ether under similar conditions.

Upon completion of the above reaction, the product can be purified by distillation, extraction or precipitation, as appropriate, using conventional methods. According to this first embodiment, the reaction product contains a reactive halide group on silicon as well as unsaturated functionality (or heterocyclic functionality) at opposite ends of its molecule. Therefore, it finds utility as a co-monomer in the preparation of silyl-functional polymers via free-radical polymerization of monomers such as methyl acrylate and styrene, or in the preparation of heterocyclic-functional siloxane polymers, inter alia. Additionally, these products may be used to end-cap anionic living siloxane polymers to prepare vinyl-functional silicone macromonomers.

In a second embodiment of the present invention, cyclic silyl ether (A) is reacted with an acyl halide of the formula

wherein G is an m-valent organic group selected from hydrocarbyl groups or heterocyclic groups containing one or more hetero atoms selected from oxygen, nitrogen or sulfur with the proviso that these heterocyclic groups do not react with component (A). In formula (ii), X is as defined above and m is at least 2. There is no particular limitation on the size of group G and it may be a low molecular weight species such as alkylene, arylene or halogen-substituted versions of these two types, preferably having 6 to 20 carbon atoms. Examples of low molecular weight G groups wherein m=2 include methylene, ethylene, propylene, butylene, isobutylene, hexylene, phenylene and naphthylene. Specific compounds wherein m=2 include oxaloyl chloride, adipoyl chloride, terephthaloyl chloride, 2,5-thiophene diacid chloride and 2,6-pyridinedicarbonyl dichloride. Examples of component (ii) wherein m=3 and m=4, respectively, are represented by the following two formulas

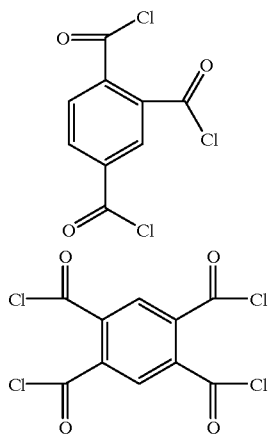

A preferred low molecular weight divalent acyl halide according to the second embodiment of the instant method is selected from adipoyl chloride or terephthaloyl chloride.

It is also contemplated that G in formula (ii) can be a polymeric group having a valence of at least 2, these materials also being known in the art. Thus, for example, carboxylic acid-ended polyesters (i.e., m=2) can be converted to polymeric acyl halides by reacting with an inorganic acid halide such as phosphorous trichloride, phosphorous pentachloride or thionyl chloride. Similarly, higher values of m can be achieved by the above described conversion of carboxyl-grafted polymers to the corresponding polymeric acyl halides. For example, poly(acrylic acid) or poly(methacrylic acid) can be so reacted to provide a polymer having a plurality of acyl halide groups pendant to the main chain.

The reaction between components (A) and (ii) can again be carried out either neat or in an organic solvent and the product subsequently purified, as described in connection with the first embodiment. In this case, however, components (A) and (ii) are reacted in a ratio designed to leave at least one equivalent of acid halide on the product and the respective amounts can readily be determined by routine experimentation. For example, when m=2 (e.g., adipoyl chloride), one mole of (A) is preferably reacted with approximately one mole of (ii); when m=3, one or two moles of (A) are reacted with about one mole of (ii), and so on.

The low molecular weight reaction products according to the second embodiment find utility as, e.g., difunctional (i.e., m=2) monomers which can be used in the synthesis of thermoplastic copolymers. For example, an acid-functional or ester-functional disiloxane can be prepared by hydrolysis or alcoholysis of the above reaction product. The resulting end-capping agent can be equilibrated with a diorganocyclopolysiloxane (e.g., in the presence of acid or base catalyst) to prepare acid-functional or ester-functional telelechelic siloxane polymers. Such telechelic systems can be subsequently reacted with organic diols or diamines to provide silicone-organic copolymers (e.g., silicone-polyesters or silicone-polyamides). Products wherein m=3, 4 could be utilized after complete alcoholysis (e.g., with methanol) to prepare pendent ester-functional siloxanes (i.e., by condensation with SiOH ended siloxanes) or to prepare pendent alkoxysilyl-functional polyamides via reaction with organic diamines.

Polymeric systems according to the second embodiment contain reactive silyl functionality as well as acyl halide functionality and can be used to modify functional polymers such as polyesters and polyamides. Further, the latter systems can be employed as surface modifying additives for paints and coatings.

In a third embodiment of the present invention, the cyclic silyl ether is reacted with a halogen-containing organophosphorous compound having a formula selected from

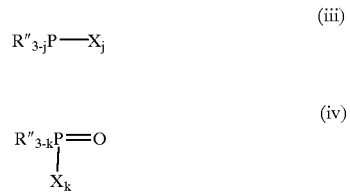

or wherein R" is independently selected from hydrocarbyl groups or halogen-substituted hydrocarbyl groups having 1 to 20 carbon atoms, j is an integer having a value of 1 to 3, k is an integer having a value of 1 to 3 and X is halogen, again preferably chloride. In the above formulas, R" can be alkyl, alkenyl, cycloalkyl, aryl, arylalkyl, alkylaryl, or halogen-substituted versions thereof. Specific non-limiting examples of R" groups include methyl, ethyl, propyl, isopropyl, butyl, tert-butyl, pentyl, cyclopropyl, cyclopentyl, vinyl, allyl, hexenyl, benzyl, beta-phenylethyl, gamma-tolylpropyl, phenyl, tolyl, xylyl, naphthyl, chloropropyl, 3,3,3-trifluoropropyl, perfluoropropyl, chlorophenyl, pentafluorophenyl and nonafluorobutyl. It is preferred that R" is selected from alkyl groups having 1 to 10 carbon atoms, alkenyl groups having 2 to 20 carbons or aryl groups having 6 to 10 carbons.

Compounds represented by formulas (iii) and (iv) are known in the art and preferred compounds according to the third embodiment include the following structures $PCl_3$, $PBr_3$, $(i-Pr)_2PCl$, $PhPCl_2$, $Ph_2PCl$, $P(O)Cl_3$, $Ph_2P(O)Cl$ and $MeP(O)Cl_2$, wherein Ph and i-Pr hereinafter denote phenyl and isopropyl groups, respectively.

The reaction between components (A) and any of the compounds (iii) and (iv) can be carried out either neat or in an organic solvent and the product subsequently purified, as described in connection with the first embodiment. In this case, component (A) and component (iii) or (iv) are combined in a ratio designed to react at least one equivalent of halide group. As before, it is preferred to use an excess of up to about 25% of component (iii) or (iv) with respect to component (A) in the above described reaction.

The products according to the third embodiment find utility, e.g., in the preparation of supported catalysts, as adhesion promoters or as hydrosilylation cure inhibitors/modifiers. For example, they can be co-hydrolyzed with silicon tetrachloride in the presence of silica or reacted as a slurry with silica in the presence of a base.

In a fourth embodiment of the present invention, the cyclic silyl ether is reacted with a halogen-functional organosulfur compound having a formula selected from

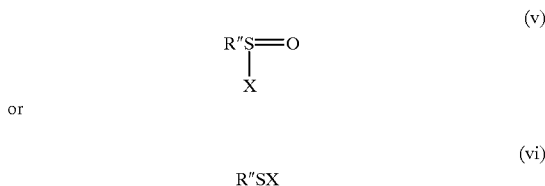

or wherein R" and X have their previously defined meanings. In this embodiment, it is preferred that R" is selected from alkyl groups having 1 to 10 carbon atoms, phenyl or tolyl and X is chlorine. Compounds represented by formulas (v) and (vi) are known in the art and can be illustrated by the following structures:

PhS(O)Cl, CF$_3$S(O)Cl, n-BuSCl, PhSCl and MeSCl, wherein n-Bu hereinafter denotes n-butyl.

The reaction between components (A) and compound (v) or (vi) can be carried out either neat or in an organic solvent and subsequently purified, as described in connection with the first embodiment. In this case, component (A) and component (v) or (vi) are reacted in an equimolar ratio and, as before, it is preferred to use an excess of up to about 25% of component (v) or (vi) with respect to component (A). Here it was again surprisingly observed that closely related halogen-functional organosulfur compounds, such as benzenesulfonyl chloride, did not react with the cyclic silyl ether.

The products of the fourth embodiment find utility in the preparation of supported catalysts and as hydrosilation cure inhibitors/modifiers.

EXAMPLES

The following examples are presented to further illustrate the method of this invention, but are not to be construed as limiting the invention, which is delineated in the appended claims. All parts and percentages in the examples are on a weight basis and all measurements were obtained at 25° C. unless indicated to the contrary.

Example 1

A 250 mL, 3-necked flask fitted with a magnetic stirrer, addition funnel, nitrogen inlet and reflux condenser was charged with 32.51 g (0.25 mole) of 2,2,4-trimethyl-1-oxa-2-silacyclopentane. The flask was heated to 60° C. under nitrogen and 31.42 g (0.30 mole) of methacryloyl chloride were added slowly through the addition funnel over a period of 30 minutes. After stirring for 17 hours at 60° C., the reaction was stopped by cooling the flask to room temperature. A total of 58.0 g of crude product was mixed with 0.05 g of CuCl$_2$ and distilled at 94° C/1 mm Hg to obtain 19.8 g of methacryloxyisobutyldimethylchlorosilane having a purity of 97%. The following structure was verified by $^{29}$Si nuclear magnetic resonance (NMR):

CH$_2$=C(Me)HC(O)—O—CH$_2$C(Me)HCH$_2$—Si(Me$_2$)Cl

Example 2

A 250 mL, 3-necked flask fitted with a magnetic stirrer, a nitrogen inlet and a reflux condenser was charged with 14.44 g (0.11 mole) of 2,2,4-trimethyl-1-oxa-2-silacyclopentane. The flask was heated to 54° C. under nitrogen and 31.56 g (0.13 mole) of diphenylphosphinic chloride were injected. After stirring for 17 hours at 54° C., the reaction was stopped by cooling the flask to room temperature. Nearly 100% completion of the reaction resulted in the following structure, as verified by NMR:

Ph$_2$P(=O)—O—CH$_2$C(Me)HCH$_2$—Si(Me$_2$)Cl

Example 3

A 100 mL, 3-necked flask fitted with a magnetic stirrer, a nitrogen inlet and a 10 reflux condenser was charged with 5.03 g (0.037 mole) of 2,2,4-trimethyl-1-oxa-2-silacyclopentane. The flask was heated to 50° C. under nitrogen and 7.85 g (0.043 mole) of adipoyl chloride were injected. After stirring for 21 hours at 50° C., the reaction was stopped by cooling the flask to room temperature. Nearly 100% completion of the reaction resulted in the following structure, as verified by NMR:

ClC(O)—CH$_2$CH$_2$CH$_2$CH$_2$—C(O)—O—CH$_2$C(Me)HCH$_2$—Si(Me$_2$)Cl.

(Comparative) Example 4

A 250 mL, 3-necked flask fitted with a magnetic stirrer, a nitrogen inlet and a reflux condenser was charged with 4.06 g (0.031 mole) of 2,2,4-trimethyl-1-oxa-2-silacyclopentane. The flask was heated to 60° C. under nitrogen and 6.63 g (0.038 mole) of benzenesulfonyl chloride were injected. After stirring for 20 hours at 60° C., the reaction was stopped by cooling the flask to room temperature. No reaction occurred as evidenced by NMR analysis.

(Comparative) Example 5

A 100 mL, 3-necked flask fitted with a magnetic stirrer, a nitrogen inlet and a reflux condenser was charged with 5.80 g (0.045 mole) of 2,2,4-trimethyl-1-oxa-2-silacyclopentane. The flask was heated to 50° C. under nitrogen and 5.84 g (0.048 mole) of allyl chloroformate were injected. After stirring for 17 hours at 50° C., the reaction was stopped by cooling the flask to room temperature. No reaction occurred as evidenced by NMR analysis.

(Comparative) Example 6

A 250 mL, 3-necked flask fitted with a magnetic stirrer, a nitrogen inlet and a 5 reflux condenser was charged with 32.60 g (0.25 mole) of 2,2,4-trimethyl-1-oxa-2-silacyclopentane. The flask was heated to 40° C. under nitrogen and 23.41 g (0.31 mole) of allyl chloride were injected into the flask. After stirring for 21 hours at 40° C., the reaction was stopped by cooling the flask to room temperature. No reaction occurred as evidenced by NMR analysis.

That which is claimed is:

1. A method for preparing a functional halosilanes by reacting (A) a cyclic silyl ether having a formula selected from the group consisting of

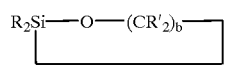

wherein each R is independently selected from a hydrocarbyl group or a halogen-substituted hydrocarbyl group having 1 to 20 carbon atoms, each R' is independently selected from a group consisting of hydrogen and R and b is 3, 4 or 5; and (B) a halogen-functional compound having a formula selected from

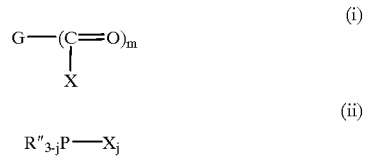

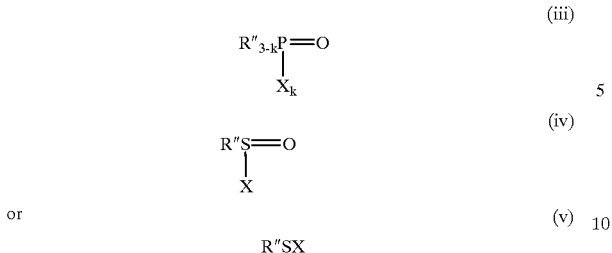

wherein G is an m-valent organic group selected from hydrocarbyl groups or hydrocarbyl groups containing at least one hetero atoms selected from oxygen, nitrogen or sulfur, m is at least 2, X is halogen, R" is independently selected from hydrocarbyl groups or halogen-substituted hydrocarbyl groups having 1 to 20 carbon atoms, j is an integer having a value of 1 to 3 and k is an integer having a value of 1 to 3.

2. The method according to claim 1, wherein X is chlorine.

3. The method according to claim 2, wherein said cyclic silyl ether has a formula selected from

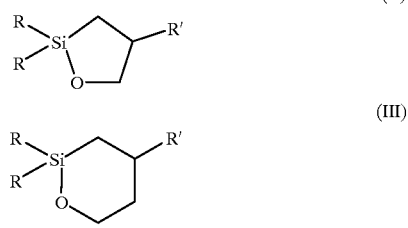

wherein each R is independently selected from methyl, phenyl or trifluoropropyl and R' is selected from hydrogen or methyl.

4. The method according to claim 3, wherein said cyclic silyl ether is 2,2,4-trimethyl-1-oxa-2-silacyclopentane.

5. The method according to claim 4, wherein said a halogen-functional compound has the formula

wherein G is an alkylene group having 6 to 20 carbon atoms.

6. The method according to claim 4, wherein said a halogen-functional compound has the formula selected from

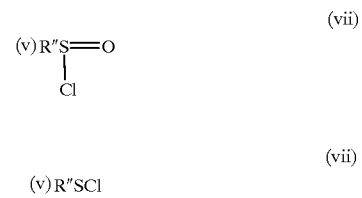

wherein R" is selected from alkyl groups having 1 to 10 carbon atoms, alkenyl groups having 2 to 20 carbons or aryl groups having 6 to 10 carbons, j is an integer having a value of 1 to 3 and k is an integer having a value of 1 to 3.

7. The method according to claim 4, wherein said a halogen-functional compound has the formula selected from $$(v) R''\underset{\underset{Cl}{|}}{S}=O \quad \text{(vii)}$$

or $$(v) R''SCl \quad \text{(vii)}$$

wherein R" is selected from alkyl groups having 1 to 10 carbon atoms, phenyl or tolyl.

8. The method according to claim 1, wherein G contains at least one hetero atom.

9. The method according to claim 8, wherein X is chlorine and said cyclic silyl ether has a formula selected from

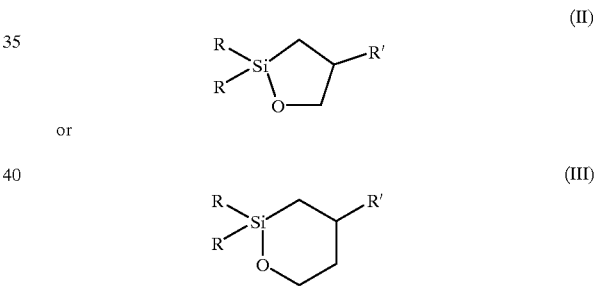

wherein each R is independently selected from methyl, phenyl or trifluoropropyl and R' is selected from hydrogen or methyl.

10. The method according to claim 9, wherein said cyclic silyl ether is 2,2,4-trimethyl-1-oxa-2-silacyclopentane.

* * * * *